United States Patent [19]

Routh et al.

[11] Patent Number: 5,800,466
[45] Date of Patent: Sep. 1, 1998

[54] DYNAMIC ATRIAL DETECTION SENSITIVITY CONTROL IN AN IMPLANTABLE MEDICAL CARDIAC SIMULATOR

[75] Inventors: Andre Routh, Lake Jackson, Tex.; Annette Bruls, Brussels, Belgium; Drury Woodson, II, Alvin; Joseph Vandegriff, Brazoria, both of Tex.; Yves Verboven, Kessel-lo, Belgium

[73] Assignee: Sulzer Intermedics Inc., Angleton, Tex.

[21] Appl. No.: 843,234

[22] Filed: Apr. 14, 1997

[51] Int. Cl.⁶ .................................................. A61N 1/362
[52] U.S. Cl. .................................................. 607/14; 607/30
[58] Field of Search .................................. 607/9, 13, 30, 607/14

[56] References Cited

U.S. PATENT DOCUMENTS

| | | | |
|---|---|---|---|
| 4,527,568 | 7/1985 | Rickards | 128/419 |
| 4,663,701 | 5/1987 | Stotts | 363/60 |
| 4,856,523 | 8/1989 | Sholder et al. | 128/419 |
| 4,903,699 | 2/1990 | Baker, Jr. et al. | 128/419 |
| 4,913,145 | 4/1990 | Stotts | 128/419 |
| 5,052,388 | 10/1991 | Sivula et al. | 128/419 |
| 5,103,819 | 4/1992 | Baker et al. | 128/419 |
| 5,190,052 | 3/1993 | Schroeppel | 128/786 |
| 5,350,409 | 9/1994 | Stoop et al. | 607/17 |
| 5,391,189 | 2/1995 | van Krieken et al. | 607/17 |
| 5,431,693 | 7/1995 | Schroeppel | 607/28 |
| 5,443,485 | 8/1995 | Housworth et al. | 607/28 |
| 5,543,795 | 8/1996 | Fernald | 341/163 |
| 5,571,144 | 11/1996 | Schroeppel | 607/28 |

OTHER PUBLICATIONS

Larry J. Stotts; Introduction to Implantable Biomedical IC Design; Jan., 1989 pp. 12–19; IEEE Circuits and Devices Magazine.

*Primary Examiner*—William E. Kamm
*Assistant Examiner*—Kennedy J. Schaetzle
*Attorney, Agent, or Firm*—John R. Merkling; Conley, Rose & Tayon

[57] ABSTRACT

An implantable medical device for electrically stimulating the heart to beat includes a sense circuit for detecting cardiac electrical activity. The sense circuit includes an amplifier with a dynamically adjustable gain to provide increased sensitivity to the electrogram during atrial fibrillation. Alternatively, sensitivity control is provided by dynamically adjusting threshold limits associated with a threshold detector included in the sense circuit. The sensitivity level of the medical device to the electrogram can be repeatedly adjusted after implantation and preferably is increased upon detection of the loss of normal sinus rhythm (NSR) in the heart's atria. The medical device is calibrated with the aid of a calibration device external to the body to determine appropriate sensitivity levels. A method for calibrating and operating an implanted medical device with dynamically adjustable sensitivity is also disclosed for improving the medical device's sensitivity to atrial fibrillation.

19 Claims, 7 Drawing Sheets

DYNAMIC ATRIAL DETECTION SENSITIVITY CONTROL IN AN IMPLANTABLE MEDICAL CARDIAC SIMULATOR

BACKGROUND OF THE INVENTION

1. Field of the Invention

The present invention relates generally to cardiac stimulating devices, such as pacemakers and defibrillators. More particularly, the present invention relates to a cardiac stimulating device that is capable of operating in multiple modes of operation. Still more particularly, the present invention relates to a cardiac stimulating device that enhances detection of atrial rhythms by dynamically controlling the device's atrial detection sensitivity.

2. Description of the Related Art

In the normal human heart, illustrated in FIG. 1, the sinus (or sinoatrial (SA)) node generally located near the junction of the superior vena cava and the right atrium constitutes the primary natural pacemaker by which rhythmic electrical excitation is developed. The cardiac impulse arising from the sinus node is transmitted to the two atrial chambers (or atria) at the right and left sides of the heart. In response to excitation from the SA node, the atria contract, pumping blood from those chambers into the respective ventricular chambers (or ventricles). The impulse is transmitted to the ventricles through the atrioventricular (AV) node, and via a conduction system comprising the bundle of His, or common bundle, the right and left bundle branches, and the Purkinje fibers. The transmitted impulse causes the ventricles to contract, the right ventricle pumping unoxygenated blood through the pulmonary artery to the lungs, and the left ventricle pumping oxygenated (arterial) blood through the aorta and the lesser arteries to the body. The right atrium receives the unoxygenated (venous) blood. The blood oxygenated by the lungs is carried via the pulmonary veins to the left atrium.

This action is repeated in a rhythmic cardiac cycle in which the atrial and ventricular chambers alternately contract and pump, then relax and fill. Four one-way valves, between the atrial and ventricular chambers in the right and left sides of the heart (the tricuspid valve and the mitral valve, respectively), and at the exits of the right and left ventricles (the pulmonic and aortic valves, respectively, not shown) prevent backflow of the blood as it moves through the heart and the circulatory system.

The sinus node is spontaneously rhythmic, and the cardiac rhythm it generates is termed normal sinus rhythm ("NSR") or simply sinus rhythm. This capacity to produce spontaneous cardiac impulses is called rhythmicity, or automaticity. Some other cardiac tissues possess rhythmicity and hence constitute secondary natural pacemakers, but the sinus node is the primary natural pacemaker because it spontaneously generates electrical pulses at a faster rate. The secondary pacemakers tend to be inhibited by the more rapid rate at which impulses are generated by the sinus node.

Disruption of the natural pacemaking and propagation system as a result of aging or disease is commonly treated by artificial cardiac pacing, by which rhythmic electrical discharges are applied to the heart at a desired rate from an artificial pacemaker. An artificial pacemaker (or "pacer" as it is commonly labeled) is a medical device which delivers electrical pulses to an electrode that is implanted adjacent to or in the patient's heart in order to stimulate the heart so that it will contract and beat at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. An in-depth explanation of certain cardiac physiology and pacemaker theory of operation is provided in U.S. Pat. No. 4,830,006.

Pacers today are typically designed to operate using one of three different response methodologies, namely, asynchronous (fixed rate), inhibited (stimulus generated in the absence of a specified cardiac activity), or triggered (stimulus delivered in response to a specified hemodynamic parameter). Broadly speaking, the inhibited and triggered pacemakers may be grouped as "demand" type pacemakers, in which a pacing pulse is only generated when demanded by the heart. To determine when pacing is required by the pacemaker, demand pacemakers may sense various conditions such as heart rate, physical exertion, temperature, and the like. Moreover, pacemaker implementations range from the simple fixed rate, single chamber device that provides pacing with no sensing function, to highly complex models that provide fully automatic dual chamber pacing and sensing functions. The latter type of pacemaker is the latest in a progression toward physiologic pacing, that is, the mode of artificial pacing that most closely simulates natural pacing.

Because of the large number of options available for pacer operation, an industry convention has been established whereby specific pacer configurations are identified according to a code comprising three, four or five letters. The fifth code position describes the antitachycardia functions, if any. Because this position is not applicable to most commonly used pacemaker types, most common codes comprise either three or four letters, as shown in the table below. For this reason and for simplicity's sake, the fifth code position is omitted from the following table. Each code can be interpreted as follows:

|  | Code position | | | |
|---|---|---|---|---|
|  | 1 | 2 | 3 | 4 |
| Function identified | chamber paced | chamber sensed | response to sensing | programmability, rate modulation |
| Options available | 0 - none<br>A - atrium<br>V - ventricle<br>D - dual<br>(A + V) | 0 - none<br>A - atrium<br>V - ventricle<br>D - dual<br>(A + V) | 0 - none<br>T - triggered<br>I - inhibited<br>D - dual<br>(T + I) | 0 - none<br>P - programmable<br>M - multi-programmable<br>C - communicating<br>R - rate modulating |

For example, a DDD pacer paces either chamber (atrium or ventricle) and senses in either chamber. Thus, a pacer in DDD mode, may pace the ventricle in response to electrical activity sensed in the atrium. A VVI pacer paces and senses in the ventricle, but its pacing is inhibited by spontaneous electrical activation of the ventricle (i.e., the ventricle paces itself naturally). In VVIR mode, ventricular pacing is similarly inhibited upon determining that the ventricle is naturally contracting. With the VVIR mode, the pacer's pacing rate, however, in the absence of naturally occurring pacing, is modulated by the physical activity level of the patient. Pacers commonly include accelerometers to provide an indication of the patient's level of physical activity.

Of the many possible pacer configurations, only four or five are commonly used today. These common configurations or modes are VVI, VVIR, DVI, DDD and DDDR. Most pacers are capable of switching between two or more of these various operational modes depending on the condition of the patient.

An exemplary rhythm of the electrical activity in the left or right atrium is shown in FIG. 2. A rhythm representing atrial electrical activity is termed an "atrial electrogram" or "AEGM". An AEGM typically is measured by implanting a pair of electrodes in the left atrium and amplifying the signal received by the electrodes. A threshold detector commonly used in pacers identifies events in the AEGM by comparing the AEGM signal amplitude to a predetermined threshold level. When the AEGM signal exceeds the threshold level, an event is registered by the pacer. The AEGM in FIG. 2 shows atrial electrical excitation during normal sinus rhythm in the left-hand side of the waveform. The electrical impulse generated by the SA node to initiate atrial contraction is detected by the atrial electrodes at events 50. Events 50 are commonly called "A waves" or "atrial senses" (AS).

Abnormal rhythms are termed arrhythmias. Tachyarrhythmias are abnormally fast rhythms. One common type of atrial tachyarrhythmia is referred to as atrial fibrillation (AF). During AF, the atria do not contract, but move very little, merely quivering. An episode of AF is shown in the right-hand side of FIG. 2. As shown the normal atrial electrogram collapses and fractionates becoming noisy. While normal sinus rhythm (NSR) includes a consistent AEGM signal, atrial fibrillation, in contrast, is described as being "irregularly irregular." Occasionally, atrial electrical activity during AF, such as at events 52, 53, may exceed the threshold level of the threshold detector and therefore be registered as an A wave by the pacer. A conventional pacer, therefore, may misinterpret these events as naturally occurring contractions of the atria. Events 52, 53, do not represent atrial contractions, however, but merely represent a random buildup of electrical activity in the atrium near the atrial electrode, characteristic of atrial fibrillation.

Detection of a rapid succession of events 53 provides an indication of atrial fibrillation. However, because of the irregular nature of the AEGM during AF, a conventional pacer may sporadically detect AF. Accurate and continuous detection of AF is frustrated further by myopotentials (i.e., electrical signals from muscle tissue) which cause noise to be superimposed on the electrogram signal. Myopotential noise generated by the pectoral muscles, for example, near which pacemakers electrodes are typically implanted, may be particularly disruptive to the normal operation of a pacemaker and even inhibit pacing when the pacer is unable to distinguish myopotential noise from AEGM signals. Accurate detection of AF is critical to prevent the pacer from inappropriately switching between operational modes, as explained below.

Many pacemakers operate in the DDD mode of operation during normal sinus rhythm as indicated in FIG. 2. In this mode, electrical excitations in the atrium are detected as atrial senses 50. Upon detection of an atrial sense, a DDD pacer waits a brief period of time T (commonly called the atrio-ventricular delay) to allow the ventricles an opportunity to fill with blood and then paces the ventricle by providing a ventricular pacing pulse (VP) through the ventricular electrodes causing the ventricle to contract. The first three events 50 in the AEGM of FIG. 2 follow this methodology.

At the onset of atrial fibrillation, the benefit of a DDD pacer (ventricular pacing following detection of A waves) to pump blood is diminished because the sensed atrial events do not represent actual atrial contractions, and because they occur at such a rapid rate that ventricular pacing in response to the rapid atrial detections is inefficient given that the ventricles do not have time to fill in the time between pacing pulses. Rapid ventricular pacing without affording the ventricles time to fill causes the patient to become breathless and lightheaded. A DDD pacer thus switches to an alternative mode such as VVIR mode when atrial fibrillation is detected. The mode switch may occur, for example, at point 55 in FIG. 2 when the pacer detects a series of atrial senses 53 in rapid succession. As explained above, a VVIR pacer paces the ventricles in response to an activity sensor which provides an estimate of metabolic demand which can be used to determine an appropriate pacing rate. The ventricular pace pulses during the VVIR mode of operation thus are disassociated from any detected atrial sense activity; that is, VP pulses are generated by the pacer at a rate determined only by the metabolic demand of the patient as estimated by the pacer's activity sensor. Once the AF ceases and NSR begins again, the pacer mode switches back to DDD mode. A pacer that detects AF sporadically throughout a continuous episode of AF will mode switch repeatedly between modes, such as DDD and VVIR modes.

Thus, although VVIR pacers normally ignore electrical activity detected by the atrial electrodes, for a variety of reasons it is important to be able to detect and monitor accurately electrical excitation in the atrium upon switching to VVIR mode. Because of the difficulty in accurately detecting AF, a pacer may unnecessarily switch between modes, such as DDD and VVIR, repeatedly over a short period of time if AF is not detected accurately. Each time the pacer mode switches, the pacing rate may change dramatically resulting from the different criteria that are used to determine the pacing rate in the various modes. Sudden rises or drops in pacing rate may be harmful to the patient causing tiredness, faintness, nausea and palpitations. Thus, while it is incumbent for a pacer to switch modes as necessary for the patient's health, mode switching must be carefully controlled to prevent repeated unnecessary mode switches. Careful and accurate monitoring of the atrial electrogram allows a pacer to switch modes appropriately.

Although various criteria have been used to detect the onset of atrial fibrillation such as high average detection rate, irregular detection of atrial fibrillation, and constantly changing signal morphology (amplitude and polarity) many problems exist making detection and accurate monitoring of atrial fibrillation difficult as discussed above. These problems have not been fully resolved by present day pacing systems. Thus, it would be desirable to provide a pacer that can switch modes of operation once normal sinus rhythm ceases, which, for example, may occur upon the initiation of atrial fibrillation. It would be further desirable to provide a pacer with an enhanced ability to detect accurately and monitor an atrial electrogram signal during periods of atrial fibrillation and to distinguish AF from other arrythmias.

SUMMARY OF THE INVENTION

Accordingly, there is herein provided an implantable medical device such as a pacemaker for electrically stimulating the heart to beat. The implantable medical device includes a sense circuit for detecting and monitoring electrical activity, or electrogram, in the atria of the heart. The sense circuit includes an amplifier, band pass filter, and threshold detector. The sensitivity level of the atrial sense circuit is adjusted and preferably increased during periods of tachyarrhythmias, such as atrial fibrillation, to provide enhanced and more accurate detection of atrial fibrillation than is provided by present pacemakers. The atrial sense circuit's sensitivity level may be controlled by varying either the gain of the atrial sense amplifier or the threshold level of the threshold detector.

The character of the atrial electrogram during normal sinus rhythm and during atrial fibrillation varies from patient to patient and thus the present invention is tailored for each patient in which the pacemaker is implanted. The medical device is adjusted during implantation or later with the aid of an external programmer. Cardiac electrical activity during normal sinus rhythm in the form of an electrogram is transmitted from the medical device to the external programmer. The external programmer determines an appropriate gain value for the atrial sense amplifier during normal sinus rhythm and a different gain value appropriate for atrial fibrillation. The gain values are then transmitted back to the pacer and used during normal operation. Alternatively, the external programmer may compute two sets of threshold values for the atrial threshold detector appropriate for normal sinus rhythm and atrial fibrillation and transmit those values to the pacer.

During operation, the medical device uses the gain or threshold values determined upon tailoring the device to the patient to set the pacer's sensitivity level during normal sinus rhythm. If atrial fibrillation is detected, the pacemaker dynamically switches to an appropriate mode of operation and increases the sensitivity of the atrial sense circuit, either by increasing the gain of the atrial amplifier to the calibration-determined value or lowering the threshold levels of the atrial threshold detector. Once atrial fibrillation ceases and normal sinus rhythm begins again, the sensitivity level of the atrial sense circuit dynamically reverts back to its normal sinus rhythm value.

BRIEF DESCRIPTION OF THE DRAWINGS

Other objects and advantages of the invention will become apparent upon reading the following detailed description and upon reference to the accompany drawings, wherein.

DETAILED DESCRIPTION OF THE INVENTION

Figure 1:
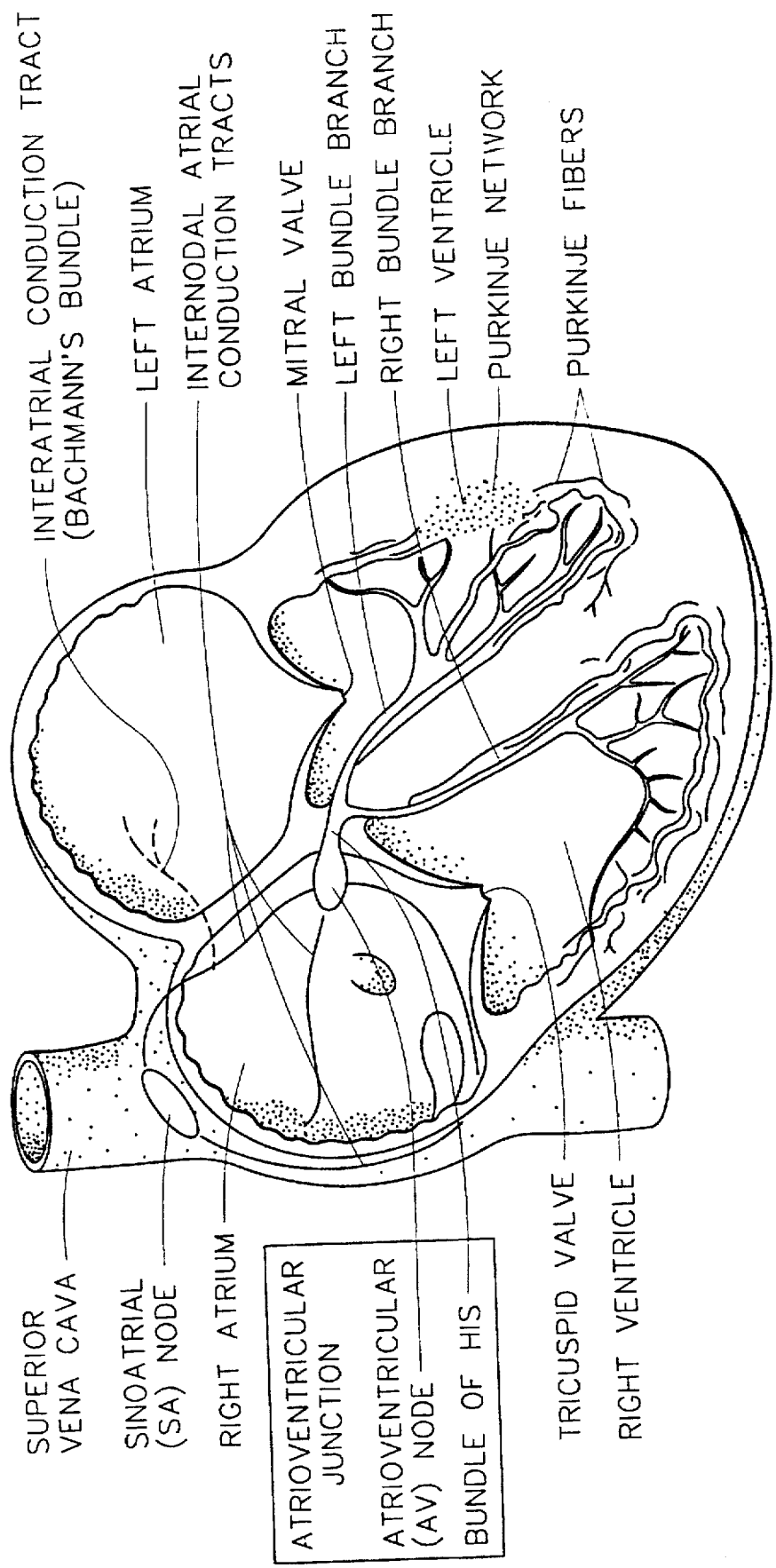
FIG. 1 is a schematic cut-away view of a human heart, in which the various relevant parts are labeled.
Figure 2:
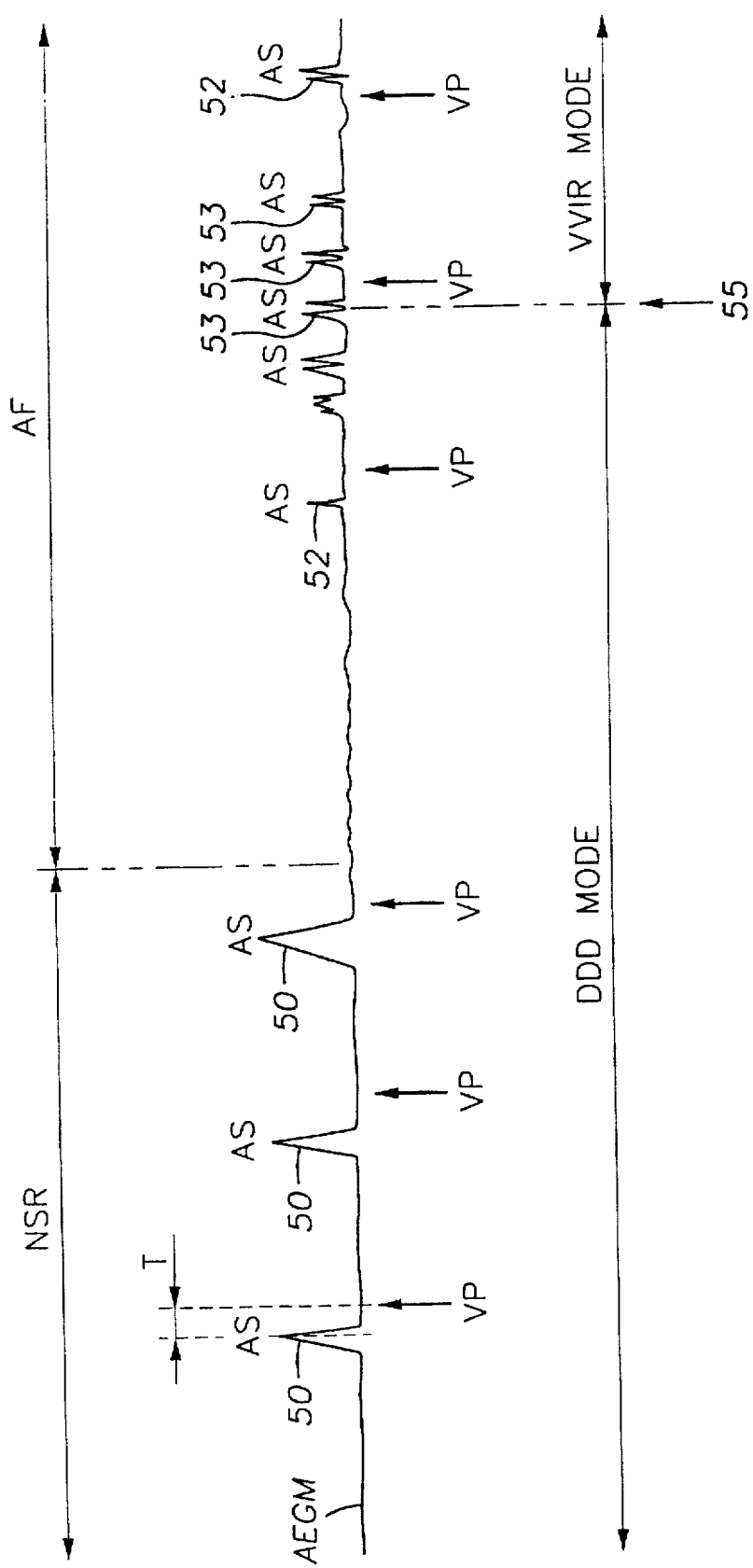
FIG. 2 shows an exemplary atrial electrogram during normal sinus rhythm and during atrial fibrillation.
Figure 3:
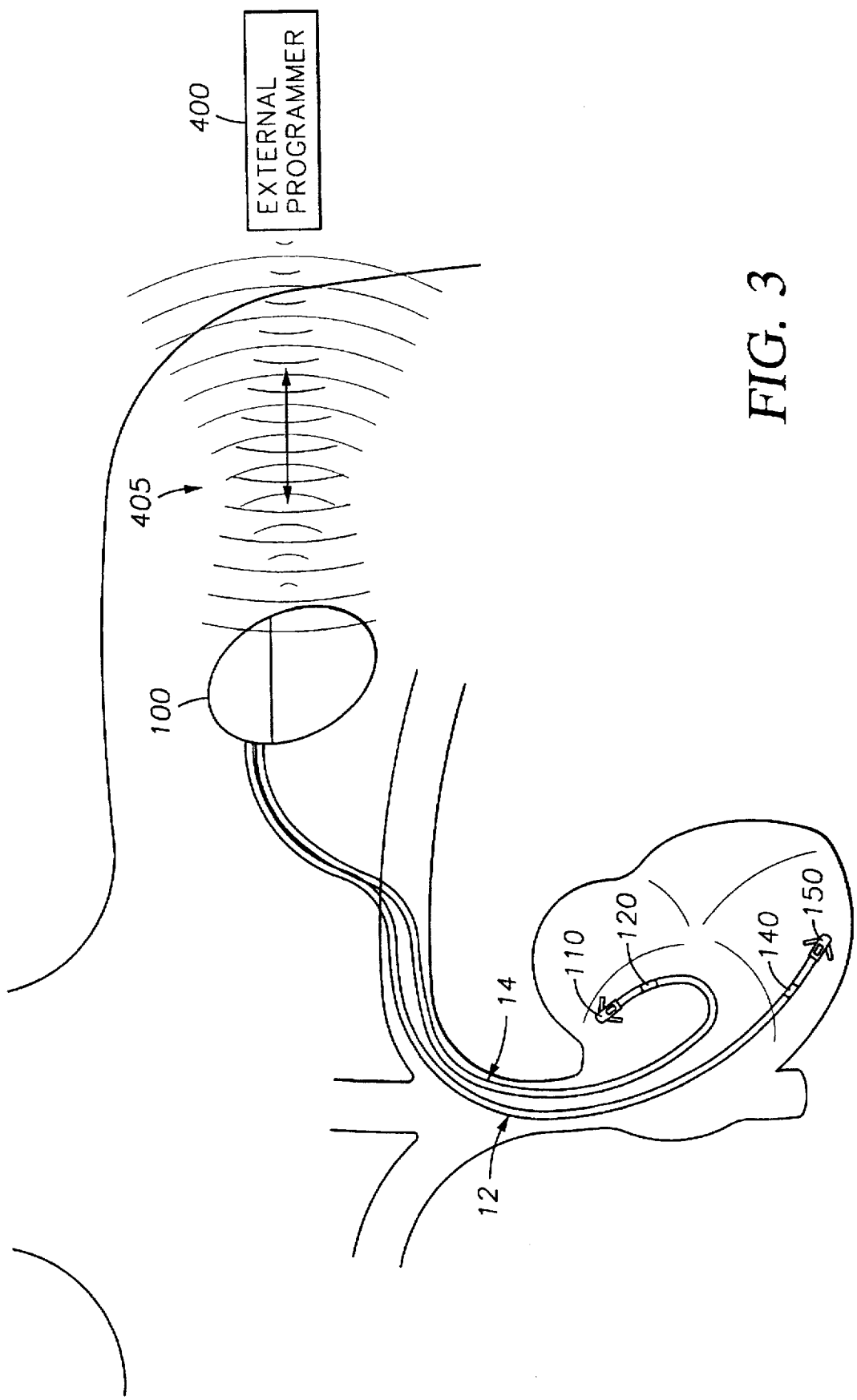
FIG. 3 is a schematic diagram of a pacer and external programmer constructed in accordance with the present invention implanted in a human body.

Referring now to FIG. 3, an implantable medical device 100 constructed in accordance with the preferred embodiment is shown implanted and coupled to the patient's heart by leads 12, 14. Medical device 100 communicates with an external programmer 400, described below. The communication path is indicated by reference numeral 405. The implantable medical device 100 may include a pacemaker or any medical device that performs pacing functions. For purposes of describing the preferred embodiments of the invention, the implantable medical device will hereafter be described as an implantable pacemaker or simply pacer 100. However, it should be understood that the invention may likewise be employed in any of a variety of implantable medical devices, such as defibrillators.

In the dual chamber pacing arrangement shown, leads 12, 14 are positioned in the right ventricle and right atrium, respectively. Alternatively, leads could be connected to the left ventricle and left atrium. Each lead 12, 14 includes at least one stimulating electrode for delivery of electrical impulses to excitable myocardial tissue in the appropriate chamber(s) in the right side of the patient's heart. As shown in FIG. 3, each lead 12, 14 includes two electrodes. More specifically, lead 14 includes tip electrode 110 and ring electrode 120, and lead 12 includes tip electrode 150 and ring electrode 140. As one skilled in the art will understand, two, three, and four terminal devices all have been used or suggested as possible electrode schemes and may be employed in the present invention.

Figure 4:
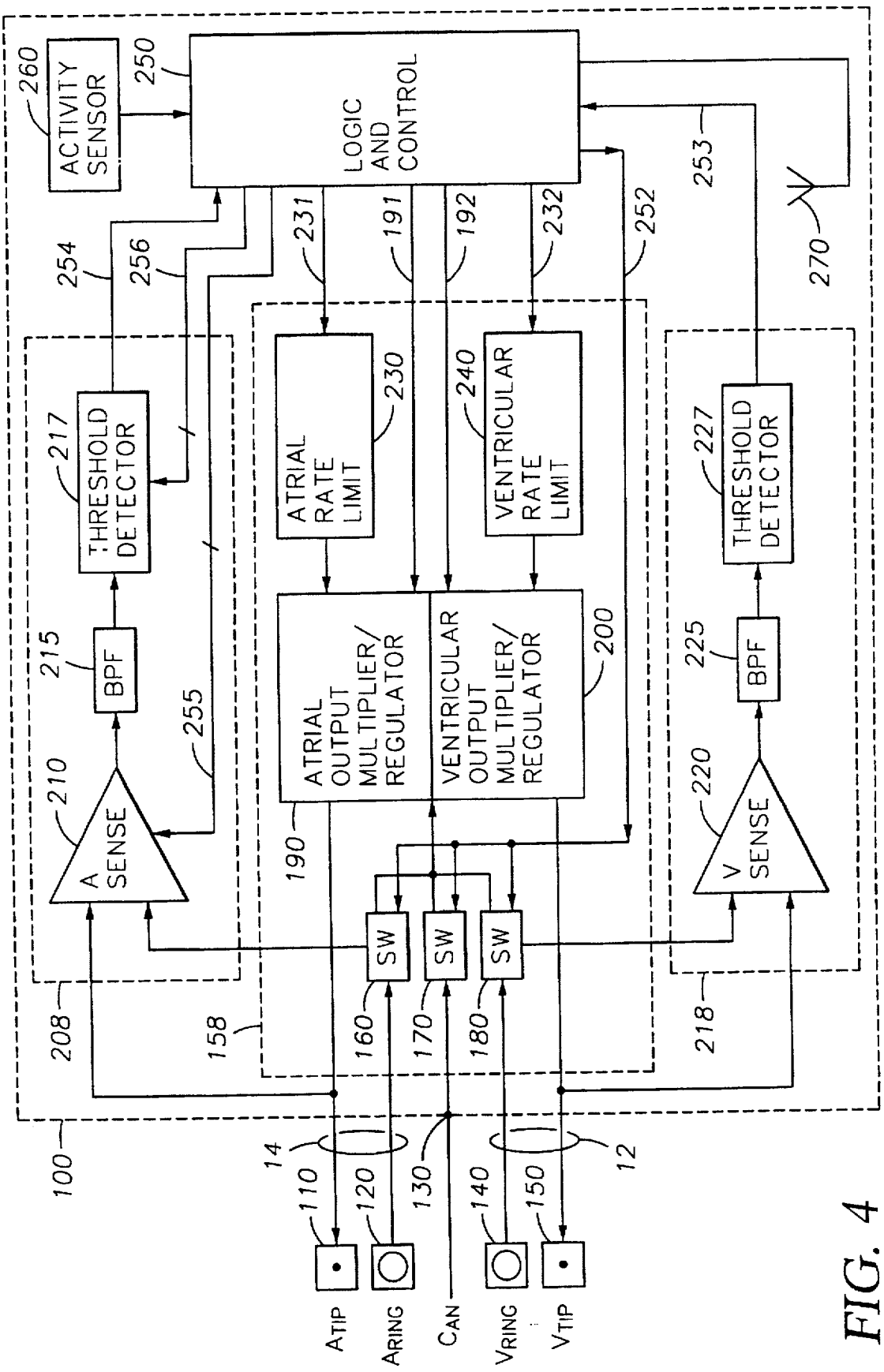
FIG. 4 is a block diagram of the pacer of FIG. 3 showing an atrial sense circuit with dynamically adjustable sensitivity.

Pacer 100 includes housing or can 130 that houses a conventional battery (not shown), pacing circuit 158, atrial sense circuit 208, ventricular sense circuit 218, logic and control unit 250, activity sensor 260, and telemetry unit 270, best shown in FIG. 4. Can 130 preferably is made of titanium, or another biocompatible conducting metal.

Referring to FIG. 4, pacing circuit 158 delivers the appropriate atrial or ventricular pacing pulses as initiated by logic and control unit 250 to the heart generally through one or more electrodes 110, 120, 140, 150 or can 130. Electrodes 110, 120, 140, 150, can 130 are also employed for sensing atrial and ventricular contractions, as explained below.

Atrial sense circuit 208 provides an indication on line 254 to logic and control unit 250 when the atrium contracts. Similarly, ventricular sense circuit 218 indicates to logic and control unit 250 on line 253 when the ventricles contract. Activity sensor 260 preferably includes an accelerometer and provides a signal to logic and control unit 250 from which the level of activity of the patient can be determined, according to known principles. This signal is used to estimate metabolic demand. Other types of activity sensors such as piezoelectric crystals and pressure sensors can also be used. Further, it is possible to determine activity level without a dedicated activity sensor through the use of known techniques such as Q-T interval and estimating minute ventilation from electrical impedance. Thus, the invention may use an activity sensor or may alternatively determine activity level through other means.

Telemetry unit 270 allows two-way communication between pacer 100 and a device external to the body such as external programmer 400 (FIG. 3). Communication may be in accordance with any one of a variety of known techniques such as transcutaneous energy transmission which employs a pair of coils of conductors, one located external to the body and the other implanted. An example of transcutaneous energy transmission is disclosed in U.S. Pat. No. 5,411,537, which is incorporated herein by reference. Telemetry unit 270 may be located within can 130 are shown in FIGS. 3 and 4, or may be separately implanted outside the can and coupled to pacer 100 through electrical conductors.

Logic and control unit 250 generally controls the operation of pacer 100 and determines when to stimulate the atria and ventricles to contract. Pacer 100 preferably also includes a memory device such as random access memory (RAM) for storing a variety of information such as heart rate data and other physiological information, status and configuration information pertaining to the operation of the pacer, and the like. Such RAM preferably is provided in the logic and control unit 250 and thus is not specifically shown. A suitable control unit 250 includes a microprocessor controller such as the Intel 8051.

Pacing energy is delivered to the heart through the electrodes in a variety of modes or configurations using logic and control unit 250 and pacing circuit 158. Pacing circuit 158 preferably includes switches 160, 170, 180, atrial and ventricular output multiplier/regulators 190, 200, and atrial and ventricular rate limiters 230, 240. Logic and control unit 250 provides pacing pulses to the rate limiters 230, 240 via lines 231, 232, respectively, and controls the state of switches 160, 170, 180 via lines 252. Although logic and control unit 250 determines when to pace the atria and/or ventricles, rate limiters 230, 240 ensure that the cardiac chambers are not paced at a rate in excess of an upper limit encoded into the rate limiters. The rate limiters, therefore, provide extra protection against pacing the heart at an excessively high rate. Rate limiters are known by those of ordinary skill in the art.

A signal substantially equivalent to the voltage of the pacer's battery (not shown), which is between approximately 2 and 3 volts (preferably 2.8 volts), is delivered to one of the output multiplier/regulators 190, 200 corresponding to the chamber to be paced as determined by logic control unit 250. Thus, if it is desired to pace the atria, logic and control unit 250 delivers a pulse to atrial output multiplier/regulator 190, the pulse rate limited by atrial rate limiter 230. Similarly, to pace the ventricle, logic and control unit 250 delivers a pacing pulse to ventricular output multiplier/regulator 200 is limited by ventricular limiter 240. Output multiplier/regulators 190, 200 preferably increase or decrease the magnitude of the voltage received from the logic and control unit 250. Output multiplier/regulators 190, 200 convert the pulse received from logic and control unit 250 through the rate limiters 230, 240 to a voltage level sufficient to cause the chambers to contract, commonly called "capture". The magnitude of the voltage output by the output multiplier/regulators 190, 200 necessary for proper pacing depends on various factors known to those of ordinary skill in the art such as which chamber is being paced, electrode placement within the chamber, and the physiology of the patient's heart. Output multiplier/regulator/regulators 190, 200 also control the width or duration of the pulse delivered to the heart and are known by those of ordinary skill. The width of the output pulses to the heart are specified by the logic and control unit 250 over control lines 191, 192.

Output multiplier/regulators 190, 200 provide pacing pulses to the heart through electrodes 110, 120, 140, 150 and can 130 and via switches 160, 170, 180. The electrodes shown schematically in FIG. 4 include two atrial electrodes (Atip 110 and Aring 120), two ventricular electrodes (Vtip 140 and Vring 150), and can 130. Can 130 represents the conducting enclosure housing the pacer's electronics as previously described. When coupled to a signal reference in the pacer, such as the positive terminal of the battery (not shown), the can is usable as a fifth electrode, as those of ordinary skill in the art will understand. Although pacer 100 is thus shown with five electrodes, any number of electrodes is consistent with the preferred embodiment.

Switches 160, 170, 180 are interposed between electrodes 120, 140 and can 130, output multiplier/regulators 190, 200, and sense amplifiers 220 of ventricular sense circuit 218. Switches 160, 170, 180, which are preferably conventional solid state switches provide the capability to support either unipolar or bipolar pacing. Pacer 100 may pace the heart in a unipolar mode in which pacing energy is delivered through either tip electrode 110 or 150 and returned through can 130. To implement unipolar mode, logic and control unit 250 opens switches 160, 180 and closes switch 170. As used herein, an "open" switch state prevents current from flowing through the switch and a "closed" switch state allows current to flow through the switch. With switch 170 closed, and switches 160, 180 open, any pacing current delivered through either tip electrode 110, 150 returns to the can 130 and not through the ring electrodes 120, 140. Thus, unipolar pacing of the atrium is achieved by delivering a pacing pulse through the Atip electrode 110 with the return current path through can 130. Similarly, the ventricle can be paced in a unipolar configuration by delivering a pacing pulse through the Vtip electrode 150 with the current path through can 130.

In a bipolar mode, a pacing pulse preferably is delivered through one of the atrial or ventricular tip electrodes 110, 150 with a return current path through one of the ring electrodes 120, 140 depending on the state of switches 160, 180. During bipolar pacing, switch 170 remains open precluding a return current path through can 130. Bipolar atrial pacing can be implemented by opening switch 160 and closing switches 170, 180. In this mode, a pacing pulse delivered to the heart through Atip electrode 110 returns through the Aring electrode 120 and switch 160. Similarly, bipolar ventricular pacing can be implemented by opening switch 180 and closing switches 160, 170 allowing a pacing pulse to be delivered to the heart through Vtip electrode 150 returns through the Vring electrode 140 and switch 180.

Pacer 100 preferably is a demand-type pacemaker and paces the heart in response to one or more physiological signals or parameters such as heart rate and activity level. To enhance detection of atrial and ventricular electrical activity, pacer 100 includes atrial and ventricular sense circuits 208, 218, respectively. Ventricular sense circuit 218 includes a sense amplifier 220, band pass filter 225, and threshold detector 227. Sense amplifier 220 amplifies the voltage across the ventricular pair of electrodes 140, 150. Sense amplifier 220 is a low power amplifier preferably operating from a power supply of approximately one microamp of current. A suitable sense amplifier is disclosed in U.S. Pat. No. 4,913,145, and incorporated herein by reference.

Band pass filter 225 preferably is a switched capacitor filter such as that disclosed in U.S. Pat. No. 4,913,145, or any other suitable low power, reliable filter suitable for use in implantable pacemakers. The transition in the frequency response of band pass filter 225 between the pass band and stop band may be gradual or sharp, depending on the number of poles included in the filter's design. The poles are the roots of the denominator polynomial of the filter's transfer function and are known by those of ordinary skill in the art. Band pass filter 225 preferably includes eight poles, although more or fewer poles are permissible.

Threshold detector 227 compares the signal provided to it by band pass filter 225 to a reference signal (not specifically shown) and provides an output signal to logic and control unit 250 on line 253. The output signal on line 253 generally indicates when the band pass filter's output signal exceeds the reference signal. The reference signal may be fixed or programmable by logic and control unit 250. The reference signal preferably is indicative of the minimum voltage level indicative of ventricular contraction. Thus, when the magnitude of the output signal of band pass filter 225 exceeds the magnitude of the reference signal, the ventricle likely is contracting. The output signal from threshold detector 227 may be encoded as a binary signal; that is, a logic high signal may indicate when the band pass filter's output exceeds the reference signal, and a logic low signal may indicate when the filter's output signal is below the reference signal.

Although the ventricular sense amplifier 220, band pass filter 225, and threshold detector 227 are shown as three separate components in the block diagram of FIG. 4, one of ordinary skill will recognize that these components may be combined into a single circuit or circuits, and this is typically the case for implantable pacemakers. For example, band pass filter 225 may be implemented using known switched capacitor technology that includes amplification for signals in the pass band of the filter. Also, ventricular sense amplifier 220, band pass filter 225, and threshold detector 227 may be provided in a different order than that shown. The arrangement of ventricular sense amplifier 220 and band pass filter 227, for example, may be reversed with band pass filter 225 coupled to the ventricular electrodes directly and then followed by ventricular sense amplifier 220.

Referring still to FIG. 4, atrial sense circuit 208 detects atrial electrical activity and comprises atrial sense amplifier 210 coupled to band pass filter 215 which couples to threshold detector 217. Atrial band pass filter 215 preferably is a switched capacitor filter of similar construction to ventricular band pass filter 225. As with the ventricular sense circuit 218, atrial sense amplifier 210, atrial BPF 215, and threshold detector 217 may be combined into a single circuit or circuits or may be provided in an order other than that shown in FIG. 4.

Figure 5:
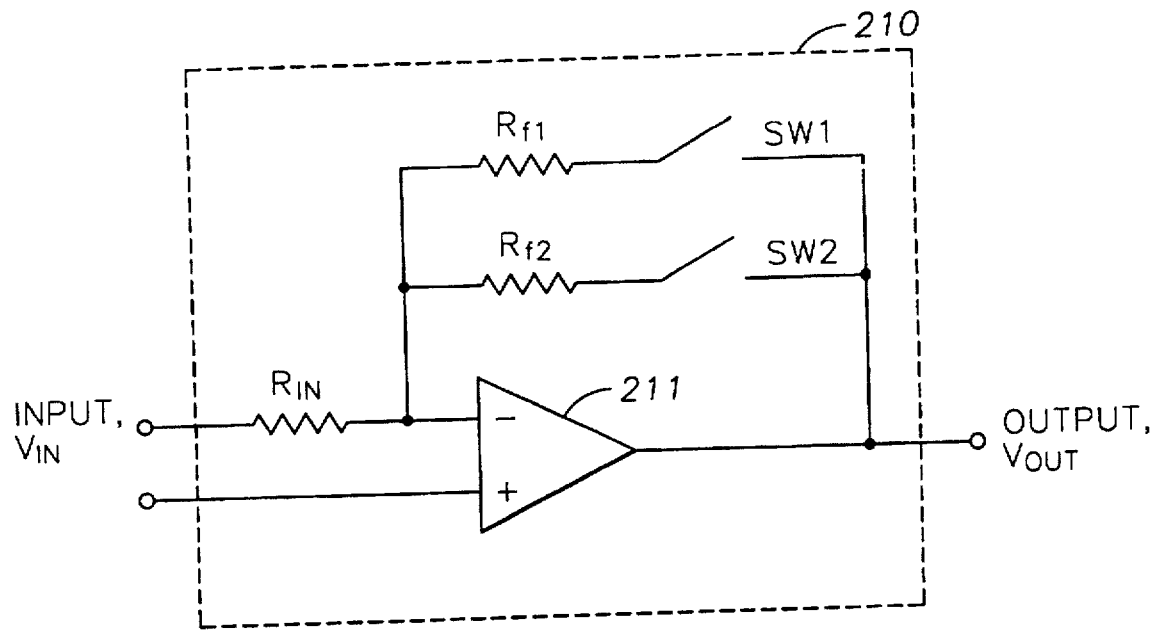
FIG. 5 shows an exemplary amplifier circuit with dynamically selectable gain for use in the atrial sense circuit of FIG. 4.

In one preferred embodiment, atrial sense amplifier 210 provides dynamic sensitivity control. Dynamic sensitivity control may be accomplished by varying the gain of the atrial sense amplifier 210 using any one of a variety of known techniques. For example, it is commonly known that the gain of an amplifier is a function of the value of the amplifier's feedback resistor. FIG. 5 shows a simple amplifier circuit intended to illustrate how the gain of atrial sense amplifier 210 can be adjusted according to the present invention. Gain generally represents the ratio of the magnitude of the output signal to the magnitude of the input signal ($V_{out}/V_{in}$). The amplifier circuit shown in FIG. 5 includes an operational amplifier 211, input resistor $R_{in}$, and feedback resistors $R_{f1}$ and $R_{f2}$. The gain of the amplifier circuit is computed as the negative ratio of the feedback resistor to the input resistor or $-(R_f/R_{in})$, where $R_f$ includes either $R_{f1}$, or $R_{f2}$. The gain value is a negative number because the amplifier circuit shown represents an inverting amplifier. The value of the feedback resistor $R_f$ depends on which switch SW1, SW2 is closed. If SW1 is closed and SW2 is open, the feedback resistor is $R_{f1}$, and if SW2 is closed (SW1 open), the feedback resistor is $R_{f1}$. The amplifier circuit shown in FIG. 5 is a simple circuit with two possible feedback resistors. Atrial sense amplifier 210 may be much more complex incorporating two or more feedback resistors and switches. Control of the switch settings is determined by logic and control unit 250 and effectuated through control signals on lines 255 (FIG. 4), as would be known by one of ordinary skill in the art. For example, it may be desired for lines 255 to include two control signals, one for each switch SW1, SW2 in FIG. 5. It should also be recognized that capacitors could be used to control the gain of amplifier 210 in a known switched capacitor configuration.

Figure 6:
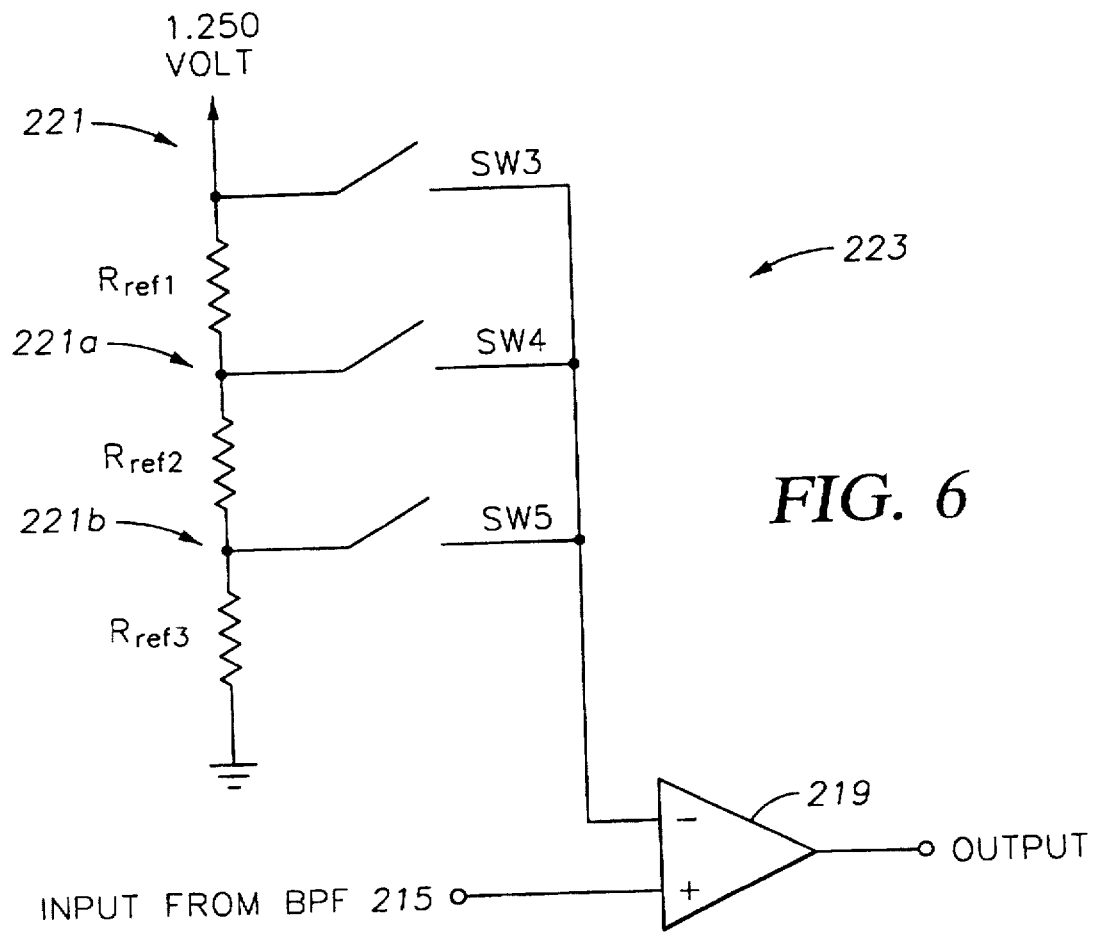
FIG. 6 shows an exemplary threshold comparator circuit with a dynamically selectable reference signal for use in the atrial sense circuit of FIG. 4.

Alternatively, dynamic sensitivity control may be provided by threshold detector 217. Threshold detector 217 generally comprises one or more comparator circuits 223 such as that shown in FIG. 6. Comparator circuit 223 includes comparator 219 which produces an output having one of two possible logic states, high or low. If the magnitude of the input signal from band pass filter 215 is less than the reference voltage on the non-inverting input (+) pin of comparator 219, the comparator's output signal will be a logic high value. If, however, the input signal from the filter 215 is greater than the reference voltage on the non-inverting pin, the comparator's output signal will be a logic low value. The reference voltage is dynamically selectable by controlling the states of switches, SW3, SW4, SW5. The state of the switches is controlled by logic and control unit 250 via control signals on lines 256 (FIG. 4), as would be known by one of ordinary skill in the art. For example, it may be desired for lines 256 to include three control signals, one for each switch SW1, SW2, SW3 in FIG. 6.

The reference voltage is selected from a voltage divider network 221 shown to comprise three resistors $R_{ref\ 1}$, $R_{ref\ 2}$, $R_{ref\ 3}$, although more or fewer resistors can be used. It should also be recognized that capacitors could be substituted for the resistors or included in a divider network having resistors and capacitors. In any event, voltage divider 221 divides a voltage, such as the 1.25 volt signal shown, into several smaller voltages at junctions 221a and 221b. The magnitude of each of the smaller voltages at junctions 221a, 221b is a function of the values of resistors $R_{ref\ 1}$, $R_{ref\ 2}$, $R_{ref\ 3}$, according to known principles. To select one of the voltages at junctions 221a, 221b, or the 1.25 volt signal, preferably one switch (SW3, SW4, SW5) at a time is closed and the other two switches remain open. Which ever switch is closed, the voltage on the junction coupling the switch is provided to the non-inverting input terminal of comparator 219 and used as the reference signal. For example, if SW4 is closed, the voltage on junction 221 a is used as the reference signal.

Broadly, according to known pacemaker methodology logic and control unit 250 monitors the output signals from atrial and ventricular threshold detectors 217, 227 to determine if the patient is experiencing NSR. This determination generally is made by computing or measuring the time between the output pulses from the threshold detectors that are produced in response to sensed detected atrial or ventricular activity. In this manner, pacer 100 can determine the rate of naturally occurring atrial and ventricular contractions and thus can estimate heart rate. During NSR, pacer 100 preferably operates in the DDD mode, as described previously. However, pacer 100 may determine that the patient is no longer experiencing NSR because the atria, for example, may be naturally contracting at an excessively high rate which may indicate atrial fibrillation. Upon detecting AF (or other tachyarrhythmias), pacer 100 preferably mode switches to VVIR mode and generally paces at a rate determined by activity sensor 260. In addition to the mode switch, logic and control unit 250 also increases the sensitivity level of atrial sense amplifier 208 to enhance detection and monitoring of the AEGM for atrial fibrillation during the VVIR mode operation. The sensitivity is increased according to either of the principles discussed above.

Figure 7:
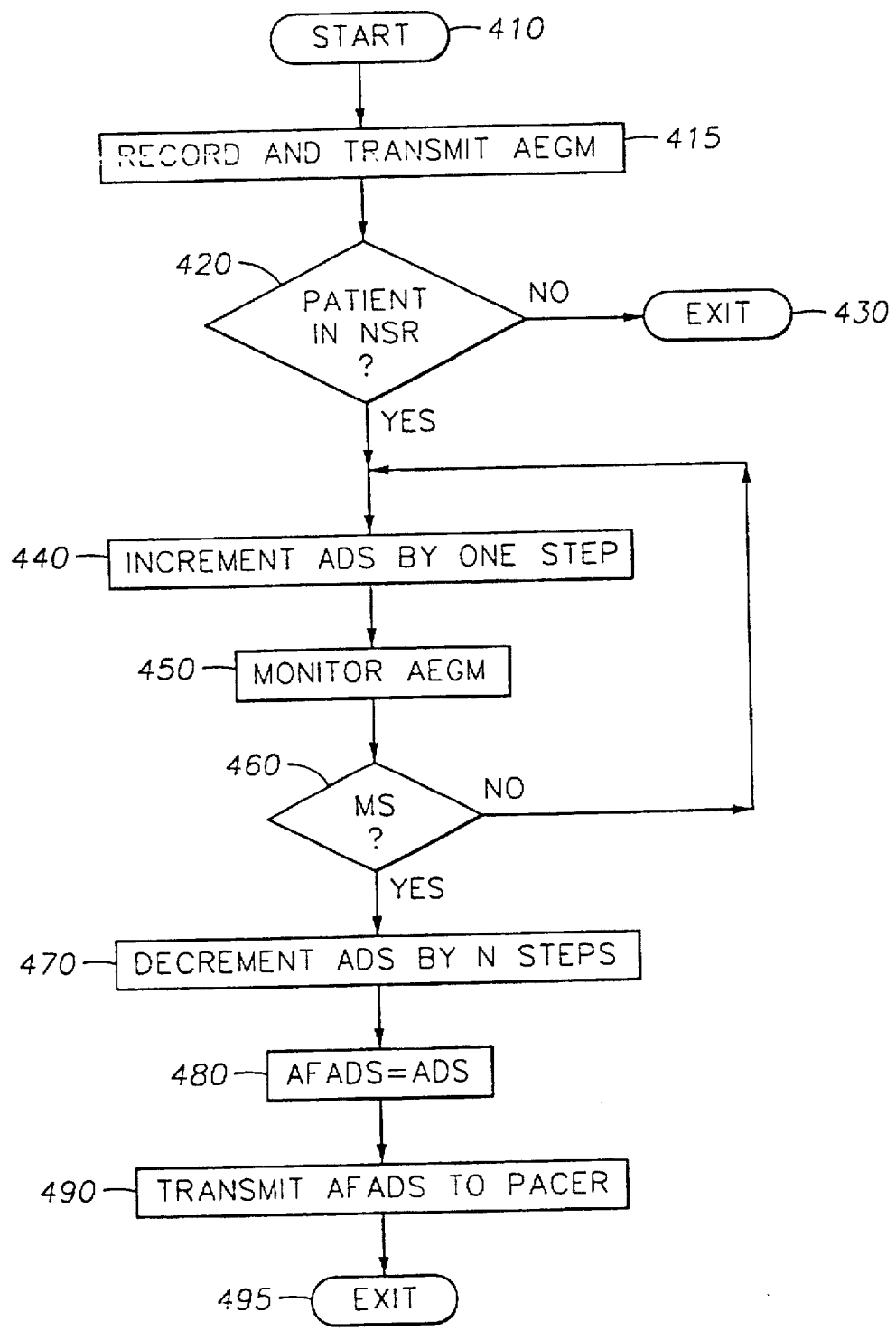
FIG. 7 is a flow chart representing the steps for tailoring the sensitivity level of the pacer of FIG. 4 to the patient.
Figure 8:
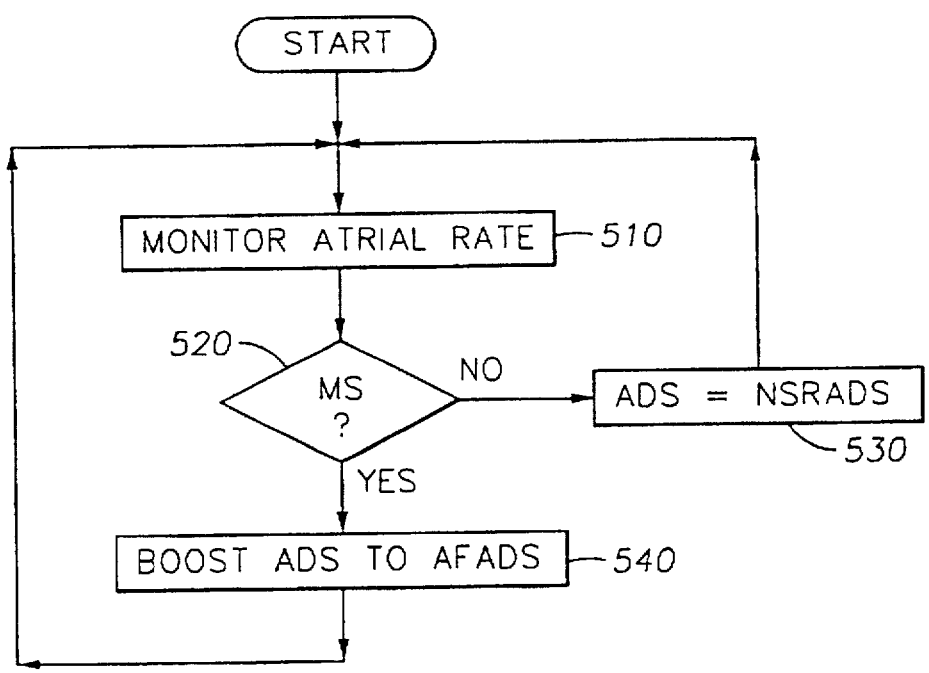
FIG. 8 is a flow chart representing the steps for controlling the sensitivity level of the pacer of FIG. 4 upon detection of a condition for switching the mode of operation of the pacer.

The operation and calibration of pacer 100 will now be described with reference to FIGS. 3, 4, 7 and 8. FIG. 7 is a flow diagram for calibrating the sensitivity level of atrial sense circuit 208 (FIG. 4) for AF using an external calibration device 400 (FIG. 3). FIG. 8 is a flow diagram for dynamically changing sensitivity level of atrial sense circuit 208 upon a mode switch as described previously.

The AEGM may vary from patient to patient depending on such factors as the unique physiology of the patient's heart and electrode location. Thus, the invention is tailored to each patient by determining a suitable sensitivity level for the atrial sense circuit 208 during atrial tachyarrythmias such as atrial fibrillation. During the tailoring routine, atrial electrogram data is transmitted from the implanted pacer 100 to external programmer 400. The external programmer 400 preferably includes a computer or any other device capable of receiving and analyzing data to design an appropriate filter for processing and enhancing the data. An acceptable programmer is model no. RX5000, manufactured by Sulzer Intermedics, Inc. Tailoring preferably is performed during the implantation procedure or during a post-operative visit to the physician's office. Telemetry unit 270 preferably allows two-way communication along communication path 405 (FIG. 3) between the implantable medical device 100 and programmer 400 as is known by one of ordinary skill in the art and described above.

Referring now to FIG. 7, the tailoring routine begins at step 410. External programmer 400 preferably initiates the tailoring routine by transmitting a start signal to pacer 100 over transmission path 405 (FIG. 3). In step 415, upon receipt of the start signal, pacer 100 records a 10–15 second sample of the AEGM and transmits the sample to external programmer 400 via telemetry unit 270 and transmission channel 405. Tailoring should be performed while the patient is experiencing NSR. Thus, in step 420, if it is determined that the patient is not in NSR (determined by examination of the transmitted AEGM), the tailoring routine aborts at step 430 and is repeated at a later time when the patient is experiencing NSR.

If the patient is in NSR, step 440 is performed in which an atrial detection sensitivity value (ADS) is incremented by one predetermined value or step. Each step may represent an incremented change in gain of atrial sense amplifier 210, an incremental threshold level charge measured in millivolts, or the like. ADS reflects the sensitivity level of atrial sense circuit 208. The ADS value is used by logic and control 250 of pacer 100 to set the gain of sense amplifier 210 or, alternatively, the threshold levels of threshold detector 217 during AF.

The external programmer 400 monitors the AEGM in step 450 and determines whether mode switch is warranted in step 460. This determination is made according to known principles, preferably using the same criteria employed by logic and control 250 of pacer 100. The criteria typically includes the occurrence of a predetermined number of atrial events within a given period of time. Whether atrial activity is detected as an event depends on the value of ADS—higher ADS values make detection more likely. Thus, if the rate of atrial detects exceeds a predetermined limit, mode switch is deemed appropriate. If, at step 460, no mode switch is warranted given the current value of ADS, control loops back to step 440 and ADS is again incremented. Steps 440, 450, and 460 are repeated, each time incrementing ADS. Eventually, for some value of ADS, mode switch will be warranted. At this point ADS has been increased to such an extent that mode switch occurs even during NSR. It is preferred that upon detection of AF, the sensitivity of the atrial detection circuit (as measured by ADS) is set as high as possible. The ADS value resulting when mode switch is deemed warranted during calibration would provide adequate sensitivity for AF, but would be so high as to unacceptably trigger mode switches during NSR. Thus, in step 470, the ADS value is decremented by n steps, thereby reducing the sensitivity level for AF to a level which will not inappropriately trigger mode switches during NSR. The value of n preferably is between 1 and 5, although n greater than 5 may be acceptable. After step completion of step 470, the value of ADS is the preferred ADS for the patient during AF, and an atrial fibrillation atrial detection sensitivity (AFADS) value is set accordingly in step 480. The value of AFADS is transmitted to the pacer and preferably is stored in the pacer's memory. Calibration ends at step 495.

Referring now to FIG. 8, the operation of pacer 100 to increase the sensitivity of pacer 100 to atrial fibrillation is shown. In step 510, the AEGM is monitored by logic and control 250. If mode switch is unnecessary in step 520, the atrial detection sensitivity level (ADS) is set in step 530 to the appropriate normal sinus rhythm atrial detection sensitivity level (NSRADS), determined during implantation. If, however, mode switch is indicated, for example due to the onset of AF, the atrial sensitivity level is increased to AFADS, the sensitivity level appropriate for AF being previously determined during calibration as described above. After steps 530 or 540, control loops back to step 510 when the AEGM again is monitored. Thus, the patient's AEGM is continuously monitored and the sensitivity level of pacer 100 is dynamically adjusted depending on whether mode switch is necessary.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A medical device for electrically stimulating the heart, comprising:

a logic and control unit for initiating a pacing pulse to be delivered to the heart;

memory for storing an atrial fibrillation atrial detection sensitivity value;

an output multiplier/regulator coupled to said logic and control unit, said output multiplier/regulator receiving said pacing pulse from said logic and control unit and altering the magnitude of the pacing pulse;

a plurality of electrodes coupled to said multiplier/regulator for applying said pacing pulse to the heart; and a sense circuit including
   a sense amplifier,
   means for dynamically adjusting gain, and
   means for providing to said logic and control unit an electrical signal indicative of electrical activity in a predetermined chamber of the heart, said logic and control unit having means responsive to said electrical signal for switching modes, said logic and control unit dynamically adjusting gain of said sense amplifier upon a mode switch.

2. The medical device of claim 1 wherein said logic and control unit further comprises means for producing a control signal and said dynamically adjustable gain of said sense amplifier is adjusted in response to said control signal from said logic and control unit.

3. The medical device of claim 2 wherein said sense circuit includes a plurality of feedback resistors coupled to said amplifier by a plurality of switches, and wherein said logic and control unit dynamically controls the state of said plurality of switches through said control signal.

4. The medical device of claim 2 wherein said sense circuit includes a plurality of capacitors coupled to said amplifier by a plurality of switches, and wherein said logic and control unit controls the state of said plurality of switches (controlled) through said control signal.

5. A medical device for electrically stimulating the heart, comprising:

a logic and control unit for initiating a pacing pulse to be delivered to the heart;

memory for storing an atrial fibrillation atrial detection sensitivity value;

an output multiplier/regulator coupled to said logic and control unit, said output multiplier/regulator receiving said pacing pulse from said logic and control unit and altering the magnitude of the pacing pulse;

a plurality of electrodes coupled to the multiplier/regulator for applying said pacing pulse to the heart; and a sense circuit including
a threshold detector;
means for dynamically adjusting a threshold level, and means for providing said logic and control unit an electrical signal indicative of electrical activity in a predetermined chamber of the heart,
said logic and control circuit having means responsive to said electrical signal for switching modes, said logic and control unit adjusting said dynamically adjustable threshold level of said sense amplifier upon a mode switch.

6. The medical device of claim 5 wherein said logic and control unit further comprises means for producing a control signal and said dynamically adjustable threshold level of said sense amplifier is adjusted in response to said control signal from said logic and control unit.

7. The medical device of claim 6 wherein said threshold detector includes a voltage divider network including resistors with switches coupled to the junctions between said resistors in said divider network, said voltage divider network providing said threshold level, and wherein said logic and control unit dynamically controls the state of said switches through said control signal.

8. The medical device of claim 6 wherein said threshold detector includes a voltage divider network including capacitors with switches coupled to the junctions between said capacitors in said divider network, said voltage divider network providing said threshold level, and wherein said logic and control unit dynamically controls the state of said switches through said control signal.

9. A method for calibrating an implantable pacemaker to provide a sensitivity level that is appropriate for atrial fibrillation, including sensitivity level and using an external calibration device, said method comprising the steps of:

(a) transmitting an electrogram waveform from said pacemaker to said calibration device;

(b) incrementing an atrial detection sensitivity value;

(c) monitoring the electrogram waveform;

(d) determining whether the implantable pacemaker is mode switched;

(e) repeating steps (b), (c), and (d) until a mode switch is warranted;

(f) decrementing said ADS value by n steps;

(g) setting an atrial fibrillation atrial detection sensitivity value equal to the ADS value resulting from step (f); and (h) transmitting said AFADS value from said calibration device to said implantable pacemaker.

10. The method of claim 9 further comprising the step of selecting n from a range of 1 to 5.

11. A method for electrically stimulating a heart and detecting atrial fibrillation using an implantable pacemaker including a pacing circuit, sense circuit including a sense amplifier with a dynamically adjustable gain, and a logic and control unit, comprising the steps of:

(a) operating said pacemaker in a first pacing mode with said gain of said sense amplifier set to a first gain value to provide adequate sensitivity for detection of normal sinus rhythm;

(b) detecting atrial tachyarrhythmia; and (c) increasing the gain of said sense amplifier to a second gain value after detecting atrial tachyarrhythmia to provide increased sensitivity to atrial tachyarrhythmia.

12. A medical system for electrically stimulating the heart, comprising:

an implantable medical device including an atrial sense circuit with means for dynamically adjusting sensitivity of said atrial sense circuit and a telemetry unit adapted to transmit atrial electrogram data; and an externally located programmer adapted to receive transmitted electrogram data, said externally located programmer having means for determining an appropriate sensitivity level for an implantable medical device to use upon detecting atrial tachyarrhythmia.

13. The medical system of claim 12 wherein said appropriate atrial tachyarrhythmia sensitivity level is transmitted to said medical device through said telemetry unit.

14. The medical system of claim 13 wherein said medical device includes memory for storing said appropriate atrial tacharrhythmia sensitivity level.

15. The medical system of claim 14 wherein said atrial sense circuit includes a sense amplifier with a variable gain circuit to provide said dynamically adjusted sensitivity.

16. The medical system of claim 14 wherein said atrial sense circuit includes a threshold detector with a variable threshold level circuit to provide said dynamically adjusted sensitivity.

17. An implantable cardiac stimulator comprising a control circuit including memory for storing a predetermined atrial fibrillation atrial detection sensitivity value;

a pulse generator controlled by said control circuit;

a sense circuit for detecting an electrical condition of the heart, said sense circuit having an adjustable sensitivity circuit;

means responsive to said sense circuit for detecting atrial fibrillation;

means for setting said sensitivity circuit to said predetermined atrial fibrillation atrial detection sensitivity value when atrial fibrillation is detected.

18. The implantable cardiac stimulator of claim 17 further comprising means responsive to said sense circuit for switching modes upon detection of a predetermined electrical condition of the heart.

19. The implantable cardiac stimulator of claim 18 wherein said predetermined electrical condition is atrial fibrillation.

* * * * *